United States Patent
Abe et al.

(10) Patent No.: US 6,953,939 B2
(45) Date of Patent: Oct. 11, 2005

(54) TESTING APPARATUS USING SCANNING ELECTRON MICROSCOPE

(75) Inventors: Tetsuo Abe, Kanagawa (JP); Kouki Okawauchi, Kanagawa (JP); Tadashi Hattori, Kanagawa (JP); Hironori Fujita, Kanagawa (JP); Minoru Takeda, Tokyo (JP); Yuichi Aki, Tokyo (JP); Naoki Date, Tokyo (JP); Setsuo Norioka, Tokyo (JP); Toshiaki Miyokawa, Tokyo (JP); Seiichi Nakagawa, Tokyo (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 10/472,312

(22) PCT Filed: Jan. 21, 2003

(86) PCT No.: PCT/JP03/00479

§ 371 (c)(1),
(2), (4) Date: Feb. 17, 2004

(87) PCT Pub. No.: WO03/062806

PCT Pub. Date: Jul. 31, 2003

(65) Prior Publication Data

US 2004/0144928 A1 Jul. 29, 2004

(30) Foreign Application Priority Data

Jan. 21, 2002 (JP) .................... 2002-011286

(51) Int. Cl.[7] ............ G01K 5/10; G21K 5/10; G21K 7/00
(52) U.S. Cl. ............ 250/441.11; 250/492.2; 250/492.3; 250/307; 250/310
(58) Field of Search ............ 250/492.2, 441.11, 250/492.3

(56) References Cited

U.S. PATENT DOCUMENTS

| 5,103,102 A | | 4/1992 | Economou et al. |
| 6,573,511 B2 | * | 6/2003 | Sasaki et al. ........... 250/441.11 |
| 6,734,437 B2 | * | 5/2004 | Norioka et al. ........ 250/441.11 |
| 6,737,660 B2 | * | 5/2004 | Miura et al. ............. 250/492.3 |
| 2001/0052577 A1 | * | 12/2001 | Aki et al. ................ 250/492.2 |

FOREIGN PATENT DOCUMENTS

| JP | 03-008428 | 1/1991 |
| JP | 08-264606 | 10/1996 |
| JP | 2001-242300 A | 9/2001 |

* cited by examiner

*Primary Examiner*—Nikita Wells
*Assistant Examiner*—Johnnie L Smith, II
(74) *Attorney, Agent, or Firm*—Robert J. Depke; Trexler, Bushnell, Giangiorgi, Blackstone & Marr (57) ABSTRACT

A testing apparatus using a scanning electron microscope for enabling tests and measurements on any part of a test subject in a nondestructive way without being limited by a size of the test subject, which is, a testing apparatus 1 using a scanning electron microscope for performing tests and measurements on any part of a test subject in a nondestructive way by using a scanning electron microscope 6a, comprising a local vacuum formation portion 9 for forming a local vacuum region by blocking around a part to be tested of the test subject from the outside air, wherein the local vacuum formation portion comprises an exhaust portion for exhausting to form a partial vacuum region, a float means 14 for floating the whole local vacuum formation portion above the test subject by emitting a compressed gas to an outer circumference portion of the local vacuum formation portion and a length measuring means 16 for measuring a distance between the test subject and the local vacuum formation portion for controlling floating of the local vacuum formation portion by the float means.

3 Claims, 6 Drawing Sheets

TESTING APPARATUS USING SCANNING ELECTRON MICROSCOPE

This application claims priority to Japanese Patent Application No. JP2002-011286, filed Jan. 21, 2002, which is incorporated herein by reference.

TECHNICAL FIELD

The present invention relates to a testing device using a scanning electron microscope and a technique for enabling to perform tests and measurements on any part of a test subject in a nondestructive way regardless of a size of the test subject.

BACKGROUND ART

A scanning electron microscope (SEM) has been generally used as a testing device of a testing apparatus for conducting tests on a variety of products (test subjects), for example, a variety of tests on a semiconductor wafer, liquid crystal substrate, etc. in production processes.

Tests and measurements by a SEM in the above testing apparatus had to be performed by taking a test subject, such as a semiconductor wafer and a liquid crystal substrate, in a highly vacuumed vacuum chamber. This is because it is necessary to test or measure in a vacuum at the time of testing and measuring by the SEM using an electron beam so as to prevent the electron beam from scattering by collisions with gas molecules.

Note that tests conducted by using the above testing apparatus are, for example when the test subject is a semiconductor wafer, conducted at a stage of forming a resist pattern on a semiconductor wafer for improving yields and to test or measure whether the resist pattern has a predetermined shape (a width size and a length) and to inspect an existence of any lacks in the resist pattern, etc. Note that the reason why the test is conducted on the semiconductor wafer at this stage is because it is before an etching process, so that it is possible to reproduce the semiconductor wafer by removing the resist when the resist pattern has any defects.

However, in the above testing apparatus, a vacuum chamber having a capacity in accordance with a size of a test subject was necessary.

Namely, in the above testing apparatus, a test subject is loaded on a load portion of a conveying means, a position of the test subject is finely adjusted by the conveying means while checking the position by using an optical testing device, etc. and a part desired to be tested and the SEM and other testing device are aligned. Thus, the vacuum chamber is required to have a size capable of taking the test subject together with the load portion of the conveying means in a vacuum. Specifically, a load portion having an area of about four times of a surface to be tested of the test subject was necessary.

Also, in the above testing apparatus, to shorten a TAT (turn around time) of a test process including a waiting time for the test, in addition to the vacuum chamber, a load lock chamber for holding the test subject in a low vacuum state before carrying it into a highly vacuum state was also required for not carrying the test subject directly into the highly vacuum state. By taking the test subject in the load lock chamber before carrying it to the vacuum chamber, an air evacuation time can be made short at the time the test subject is taken in the vacuum chamber.

In recent years, liquid crystal substrates and semiconductor wafers as test subjects of the above testing apparatus have become larger in size, and those having a side length of 700 mm or more in the former and those having a diameter of 300 mm or more in the latter have appeared. Accordingly, when testing a semiconductor wafer having a diameter of 300 mm, the load portion of the test subject of the conveying means is required to have a space of at least a diameter of 600 mm.

Therefore, in a testing apparatus for a large-scaled test subject, a vacuum chamber having a size as explained above as well as a load lock chamber was necessary, so that there was a disadvantage that the overall apparatus became large. Also, since the vacuum chamber and the load lock chamber having a large capacity as explained above had to be evacuated by a large-scale vacuum pump every time a test subject was exchanged, it took an enormous energy and time and there was a disadvantage that a test in a short time was impossible.

Particularly, in the case of a large-scale test subject, such as a liquid crystal substrate, etc. which has rapidly become large-scaled, a load portion having an area of about four times of a surface to be tested of the test subject is necessary, so there are many problems in terms of a cost and a size as explained above to prepare a vacuum chamber having a size in accordance with the large-scaled liquid crystal substrate. Consequently, there was no other way but to conduct a so-called destructive random test by preparing a sample by cutting off a part thereof for testing, so that the test can be conducted by using a small-sized vacuum chamber.

Furthermore, in the above conventional testing apparatus, there was a disadvantage of being unable to handle a peculiarly shaped test subject which cannot be handled by making the vacuum chamber large, for example, a rolled steel plate having a several hundreds of meters and other long subjects.

DISCLOSURE OF THE INVENTION

An object of the present invention is to provide a testing device using a scanning type electron microscope capable of testing or measuring any part of a test subject in a nondestructive way regardless of a size of the test subject.

A testing device using a scanning electron microscope of the present invention is configured to comprise a scanning electron microscope for performing tests and measurements on any part of a test subject in a nondestructive way by irradiating an electron beam emitted from the scanning electron microscope on a part to be tested of the test subject without being limited by a size of the test subject, wherein the device comprises a local vacuum formation portion for locally forming a vacuum region by blocking around the part to be tested on the test subject from the outside air, and the local vacuum formation portion comprises an exhaust means for exhausting to form a partial vacuum region, a float means for floating the whole local vacuum formation portion above the test subject by emitting a compressed gas to an outer circumference portion of the local vacuum formation portion and a length measuring means for measuring a distance between the test subject and the local vacuum formation portion for controlling floating of the local vacuum formation portion by the float means.

Accordingly, according to the testing device using a scanning electron microscope of the present invention, a vacuum region can be formed locally around a part to be tested of a test subject by providing a local vacuum formation portion, so that a vacuum chamber and a load lock chamber become unnecessary and a test and measurement can be performed on any part of the test subject in a nondestructive way without being limited by a size of the test subject.

BRIEF DESCRIPTION OF DRAWINGS

FIG. 1, as well as FIG. 2 and FIG. 3, shows an embodiment of applying a testing device using a scanning electron microscope, wherein

BEST MODE FOR CARRYING OUT THE INVENTION

Below, preferred embodiments of a testing device using a scanning electron microscope according to the present invention will be explained with reference to the attached drawings. Note that in the embodiment described below, a testing device using a scanning electron microscope of the present invention is applied to a SEM testing device of a testing apparatus provided with a plurality of kinds of testing devices, wherein a test subject is a semiconductor wafer.

Figure 1:
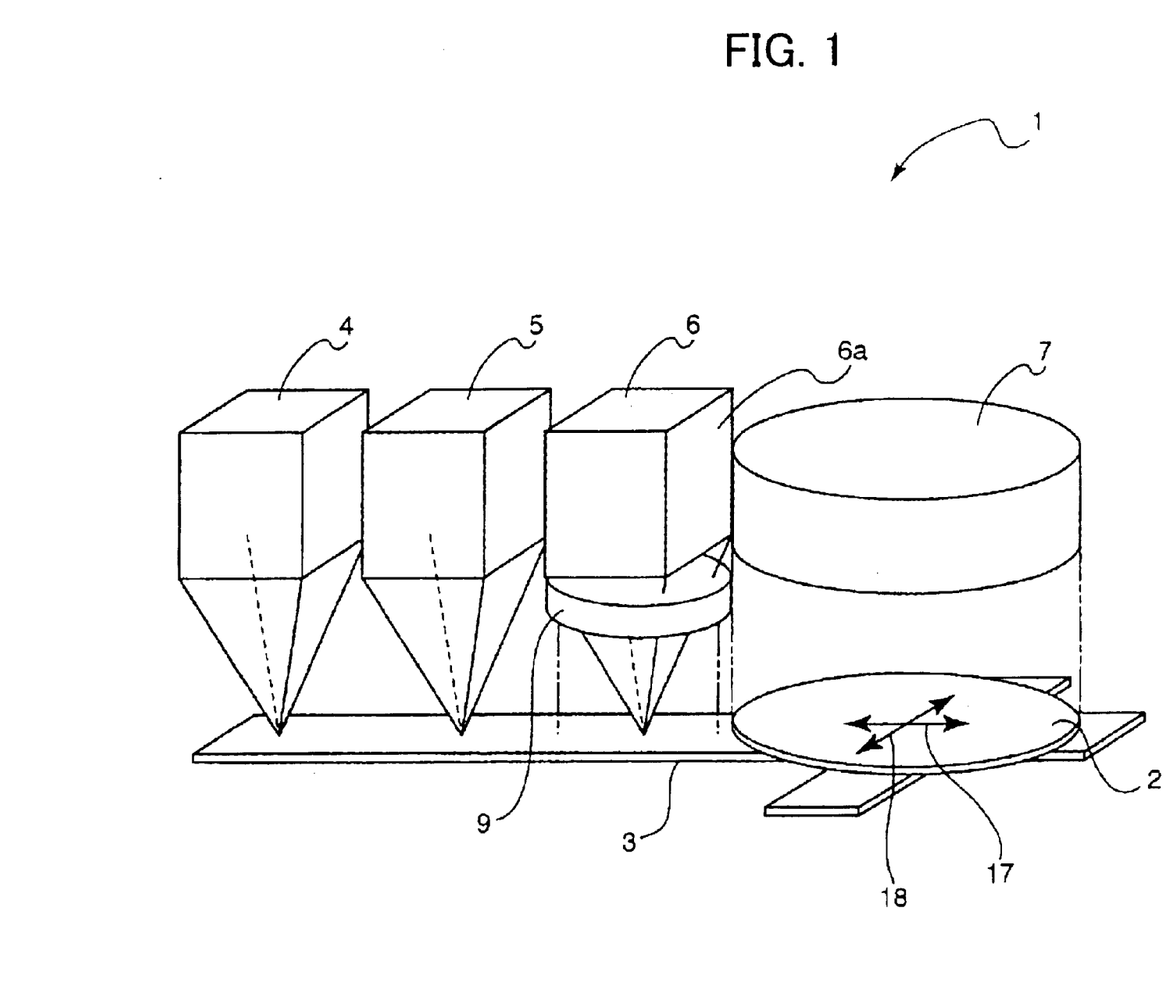
FIG. 1 is a schematic perspective view of the overall configuration of a testing apparatus of a semiconductor wafer.

A testing apparatus 1 of semiconductor wafers (hereinafter, simply referred to as a "testing apparatus") comprises, as shown in FIG. 1, one conveying portion (X–Y stage) 3 for conveying semiconductor wafers 2 as test subjects to positions to be tested respectively by a later explained variety of testing devices, a visible light testing device 4 for aligning the semiconductor wafer 2 with the conveying portion 3 when the semiconductor wafer 2 is loaded on the conveying portion 3, an optical testing device 5 for performing superposition measurements and film thickness measurements, a SEM (scanning electron microscope) testing device 6 for performing size measurements and tests of pattern defects on a resist pattern and a gate electrode pattern, etc. (hereinafter, simply referred to as a "pattern"), and an outward form testing device 7 for performing outward form tests on the overall semiconductor wafer 2, etc.

The conveying portion (conveying means) 3 has a size being able to make the semiconductor wafer 2 to face the testing devices 4, 5, 6 and 7, respectively. Accordingly, by being conveyed by the conveying portion 3, the semiconductor wafer 2 can be tested by facing to all testing devices 4, 5, 6 and 7.

Note that the "conveying portion (conveying means)" may be, for example, a multi-arm robot or other conveying means other than the X–Y stage 3 explained above. The point is those being able to convey the semiconductor wafer 2 between the respective testing devices 4, 5, 6 and 7 by one wafer conveying means and able to freely move the test subjects in a state that the test subjects face to the testing devices to perform tests and measurements can be used.

Also, loading of the semiconductor wafer 2 on the conveying portion 3 is performed by attaching a not shown wafer cassette for holding and transferring a plurality of semiconductor wafers 2 to a predetermined position of the testing apparatus 1, then, taking out one desired semiconductor wafer 2 from the wafer cassette by a suitable means.

The visible light testing device 4 is a unit for aligning the semiconductor wafer 2 with respect to the conveying portion 3, for example, by using an optical microscope. Below, an aligning operation of the semiconductor wafer 2 by the visible light testing device 4 will be explained.

First, by using an orientation flat or a notch, etc. processed on the semiconductor wafer 2 as a reference, a preliminary alignment is performed to align the direction of the semiconductor wafer 2 with the conveying portion 3.

Next, a more accurate alignment than the preliminary alignment is performed. This alignment is to align a positional coordinate system of the conveying portion 3 with a pattern positional coordinate system in the semiconductor wafer 2 and performed by using a not shown alignment pattern formed on the semiconductor wafer 2.

Namely, the above alignment is performed by comparing an optical microscopic image of an alignment pattern magnified for about several hundreds of times with a reference image of an alignment pattern registered in advance in a not shown memory unit and correcting the positional coordinates of the conveying means 3, so that the field vision exactly superposes on a field vision of the reference image.

Note that such an alignment by the visible light testing device 4 uses visible lights and an operation in the air is possible.

The optical testing device 5 uses, for example, a laser light and performs a superposition measurement for superposing and comparing a pattern stacked on the semiconductor wafer 2 with a regular pattern, an alignment measurement for inspecting whether a photomask is formed on a predetermined portion of an already formed pattern or not, or a film thickness measurement.

The optical testing device 5 optically performs tests and measurements by using a laser light, etc., which cannot be performed by an electron beam by using the later explained SEM testing device 6. Namely, tests and measurements by an electron beam by using the SEM testing device 6 are performed by picking out a secondary electron beam (a beam emitted from the outermost surface), and when testing a pattern under a film, etc., it cannot be resolved. Accordingly, the above superposition measurement, etc. are performed by an optical method using a laser light, etc. In the optical testing device 5, tests and measurements of a micron order is possible though it is not as good as performing by an electron beam. The optical testing device 5 uses an optical method as same as in the visible light testing device 4 and an operation in the air is possible.

As the optical testing device 5 for performing a superposition measurement as above, for example, there is one disclosed in the Japanese Patent Application No. 11-641.

Note that other than the above optical testing device 5, there are the visible light testing device 4 and a deep ultraviolet ray optical testing device, etc. as a testing means for optically testing by using a visible light or a laser light. The visible light testing device 4 is used in a wiring process wherein a base pattern cannot be observed by absorbing a deep ultraviolet ray of an organic low dielectric constant interlayer insulation film, etc. Also, a deep ultraviolet ray optical testing device is used when a measurement with extremely high accuracy is required as in a transistor formation process, etc.

Figure 2:
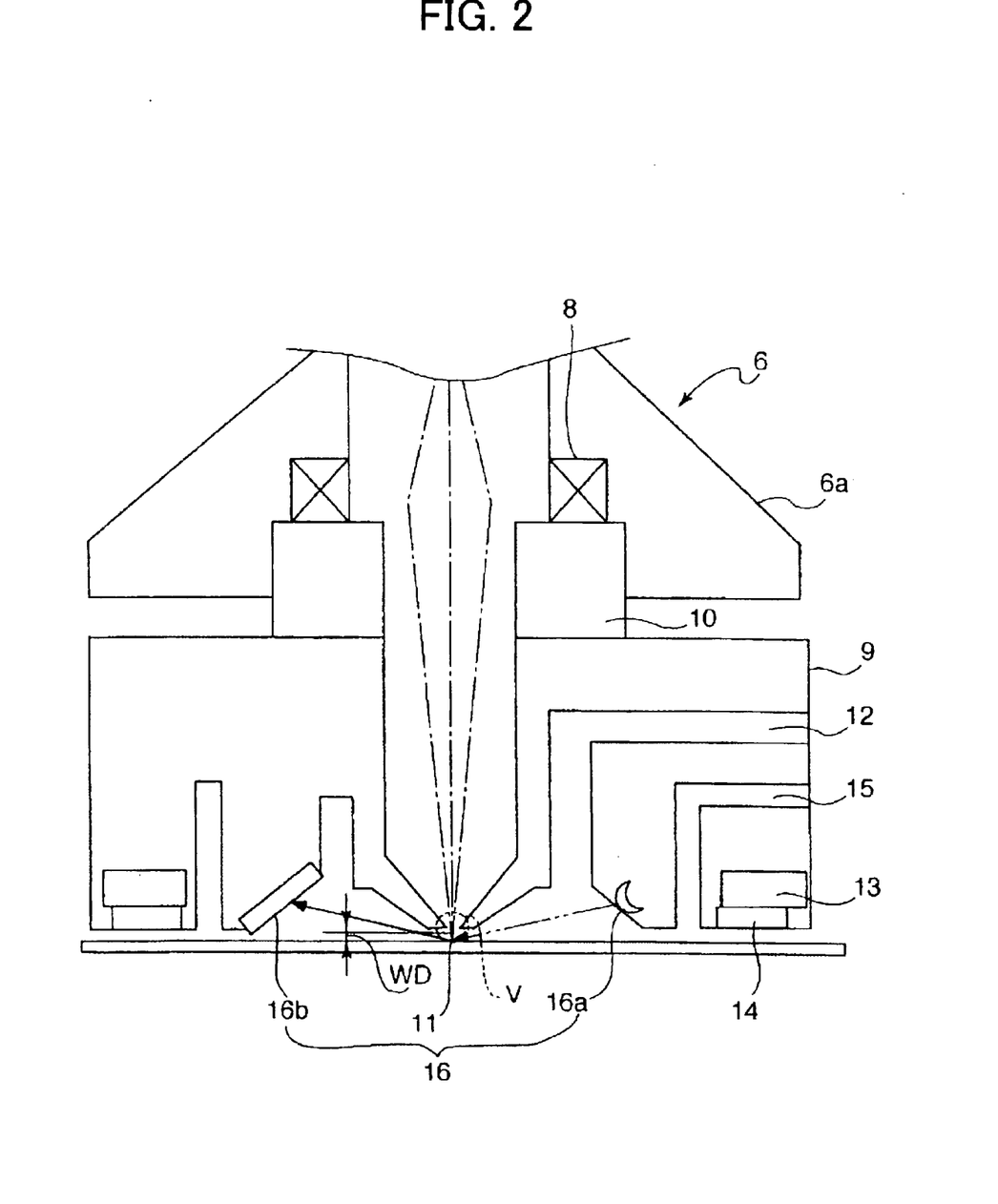
FIG. 2 is a vertical sectional view schematically showing a part of a scanning electron microscope test and a local vacuum formation portion provided thereto.

The SEM testing device 6 performs a size measurement of a resist pattern and gate electrode pattern, etc. formed on the semiconductor wafer 2 and a defect inspecting of the resist pattern and the gate electrode pattern, etc. and comprises, as shown in FIG. 1 and FIG. 2, a SEM body 6a including a not shown electron beam emission means and an object electron lens 8, etc., and a local vacuum formation portion 9 provided on a side facing to the semiconductor wafer 2 as a test subject of the SEM body 6a. The SEM body 6a and the local vacuum formation portion 9 are connected by an extendable connector (an extendable connection means) 10, such as a bellows and ricrac, as shown in FIG. 2. The reason why the SEM body 6a and the local vacuum formation portion 9 are connected by the extendable connector 10 is because the local vacuum formation portion 9 has the configuration of floating above the semiconductor wafer 2 by a later explained float portion (float means) and a positional relation with respect to the SEM body 6a is made changeable.

Tests on the semiconductor wafer 2 by the SEM testing device 6 are specifically a measurement of a width size of a pattern and a diameter of a contact hole formed on the semiconductor wafer 2 and an inspection and measurement of defects of the pattern, etc. The tests and measurements are performed in a micron order or a nano order by image processing on a visual field of 1 µm or so.

Note that the above local vacuum formation portion 9 is disclosed in detail, for example, in the Japanese Examined Patent Publication No. 6-61445 and the Japanese Patent Application No. 2000-057374, which will be simply explained below.

Namely, the local vacuum formation portion 9 comprises, as shown in FIG. 2, a first exhaust portion (exhaust means) provided around an electron beam emission hole 11 formed at the center of a surface facing to the semiconductor wafer (test subject) 2, a compressed gas supply portion (compressed gas supply means) 13, a float portion (float means) 14, a second exhaust portion (exhaust means) 15 and a length measuring portion (length measuring means) 16, etc.

As schematically shown in FIG. 2, the first exhaust portion 12 is for evacuating by exhausting around the electron beam emission hole 11, the compressed gas supply portion 13 is for supplying an inert gas, etc. to the float portion 14 provided at an outer circumference portion of a surface facing to the semiconductor wafer (test subject) 2 of the local vacuum formation portion 9, and the second exhaust portion 15 provided between the first exhaust portion 12 and the float portion 14 is for shielding so that a compressed gas supplied to the float portion 14 does not enter around the electron beam emission hole 11. Accordingly, the local vacuum formation portion 9 forms a local vacuum area V around the electron beam emission hole 11 and separates from the outside under an atmosphere pressure by the two exhaust portions 12 and 15, and floats the local vacuum formation portion 9 by the float portion 14 to secure a suitable distance WD from the surface of the semiconductor wafer 2.

Also, the length measuring portion 16 is for detecting the distance WD and comprises a laser beam emitting portion 16a for emitting a laser beam to a part to be irradiated by an electron beam on the semiconductor wafer 2 and a laser beam receiving portion 16b for receiving a laser beam reflected on the surface of the semiconductor wafer 2. The distance WD detected by the length measuring portion 16 is fed back to a control unit of the SEM body 6a, a focusing adjustment of the electron beam is performed by the object electron lens 8 and the focal position is suitably controlled to be a position corresponding to the distance WD.

The local vacuum formation portion 9 having the above configuration is attached at a lower end of the SEM body 6a as shown in FIG. 2, and thereby, a part where an electron beam (including a secondary electron beam) passes through in a space between the SEM testing device 6 and the test subject is made to be a local vacuum region V and the electron beam is prevented from scattering by colliding with gas molecules.

Also, it is configured that the SEM body 6a and the local vacuum formation portion 9 are connected by the extendable connector 10 so as to make a space between the SEM body 6a and the local vacuum formation portion 9 changeable, and the local vacuum formation portion 9 floats above the semiconductor wafer 2 as a test subject by the float means 14. Accordingly, since the SEM testing device 6 scans a surface of the semiconductor wafer 2 by a beam while floating by the extendable connector 10 and the float portion 14, it can follow fine relief shape patterns on the surface of the semiconductor wafer 2 and highly accurate tests and measurements can be performed.

Furthermore, since the semiconductor wafer 2 can be freely moved by the conveying portion 3, tests and measurements on any part of the semiconductor wafer 2 becomes possible.

A local vacuum region V can be easily realized by the local vacuum formation portion 9 as above.

Also, it is not necessary to arrange the whole SEM testing device 6 in a vacuum because the local vacuum formation portion 9 is used, accordingly, a conventionally required load lock chamber is not necessary, either. As a result, a test waiting time of the SEM testing device 6 can be made short and a testing and measuring time can be made short.

Note that in a test and measurement by the SEM testing device 6, a semiconductor wafer 2 arranged on the conveying portion 3 to face to the SEM testing device 6 is moved in the directions indicated by an arrow 17 and an arrow 18 in FIG. 1 by the conveying portion 3, so that a desired part on the semiconductor wafer 2 can be freely tested or measured. Also, a test on a part, a position of which is specified by teaching, is also possible. In this case, a test is mainly performed on a part where a performance of the semiconductor wafer 2 as a test subject is most strictly required, for example, on a line width of a gate in the case of a CPU (Central Processing Unit).

The most important process in production processes of the semiconductor wafer 2 is a lithography process and providing of such a testing process immediately after the lithography process largely affects on the yields and quality of the semiconductor wafer 2. Thus, among testing processes, a test or measurement by the SEM testing device 6 is considered to be the most important testing process in the production processes of the semiconductor wafer 2.

The outward form testing device 7 inspects an existence of defects in a macroscopic way, for example, by emitting a laser light to the semiconductor wafer 2, performing image processing on a returned light thereof to compare with a predetermined reference image and observing the whole semiconductor wafer 2. The macroscopic inspection by the outward form testing device 7 as such is able to discover a particle, scratch and unevenness, etc. which are hard to be discovered by microscopic inspections, such as the above optical test and SEM test. The outward form testing device 7 may be performed visually.

Since the outward form testing device 7 performs tests and measurements by a laser light or a visible light, so an operation in the air is possible.

In the testing apparatus 1 as above, as explained above, the semiconductor wafer 2 is tested and measured by all of the testing devices 4, 5, 6 and 7 by being conveyed by one conveying means 3. Consequently, it is not necessary to align the semiconductor wafer 2 for each of the testing devices 4, 5, 6 and 7, in the testing apparatus 1.

Also, the testing apparatus 1 is arranged in the air, and as explained above, only the SEM testing device 6 using an electron beam required to perform a test and measurement in a local vacuum region V is provided with the above local vacuum formation portion 9, and thereby, a local vacuum region V is formed in a required minimum range for the test or measurement.

Note that an arrangement of the respective testing devices 4, 5, 6 and 7 may be any as far as the semiconductor wafers 2 conveyed by the conveying means 3 can be conveyed to a position facing to the respective testing devices 4, 5, 6 and 7 and predetermined tests and measurements can be performed. A kind and arrangement of the respective testing devices 4, 5, 6 and 7 are determined by what tests and measurements are required by the semiconductor wafers 2 as test subjects.

Figure 3:
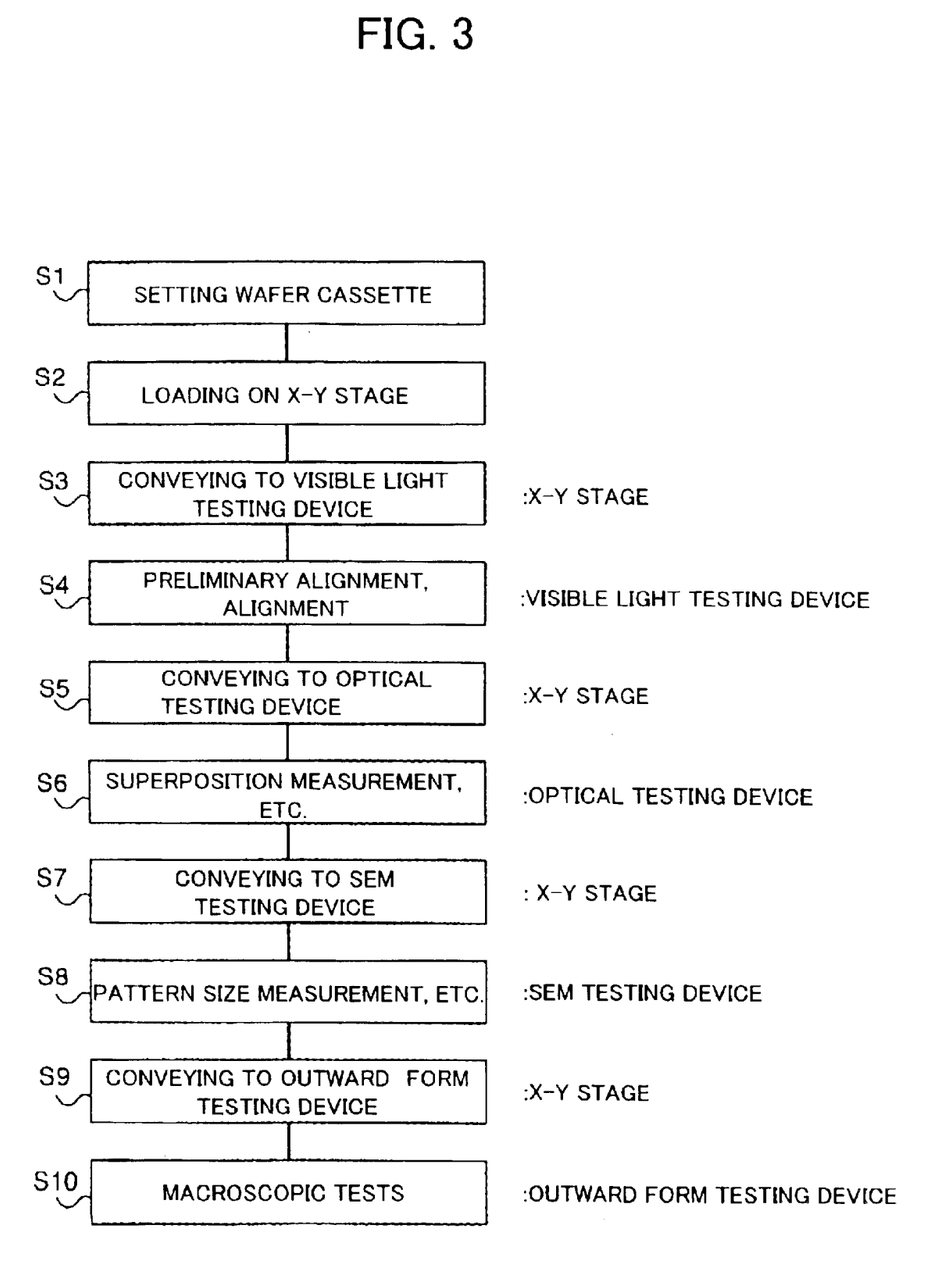
FIG. 3 is a flowchart of an example of a procedure of tests and measurements by a testing device of a semiconductor wafer.

Next, the testing processes of the semiconductor wafers 2 by the testing apparatus 1 will be explained by following the flowchart in FIG. 3 for every step in order.

Step 1: S1

A wafer cassette holding a plurality of semiconductor wafers 2 is attached to the testing apparatus 1. Note that a plurality of the semiconductor wafers 2 are held in one wafer cassette and the wafer cassette is transferred by a suitable transfer means between respective producing apparatuses or between the production apparatuses and the testing apparatus 1 in the production processes (including testing processes).

Step 2: S2

Then, when the wafer cassette is attached to the testing apparatus 1, one semiconductor wafer 2 is taken out from the wafer cassette by a not shown transfer means and loaded on the conveying portion (X–Y stage) 3.

Step 3: S3

The semiconductor wafer 2 loaded on the conveying portion 3 is conveyed to a position facing to the visible light testing device 4.

Step 4: S4

The visible light testing device 4 determines a position, that is, performs preliminary alignment and alignment of the semiconductor wafer 2 with the conveying means 3. Since the semiconductor wafer 2 is extremely accurately aligned on the conveying portion 3 thereby, it is not necessary to perform furthermore alignment in tests and measurements in stages thereafter in the testing apparatus 1.

Step 5: S5

The semiconductor wafer 2 aligned to the conveying portion 3 is conveyed by the conveying portion 3 to a position facing to the optical testing device 5.

Step 6: S6

The optical testing device 5 performs tests and measurements which cannot be performed by using an electronic beam, such as the superposition measurement and film thickness measurement explained above.

Step 7: S7

The semiconductor wafer 2 subjected to predetermined tests and measurements by the optical testing device 5 is conveyed by the conveying portion 3 to a position facing to the SEM testing device 6.

Step 8: S8

The SEM testing device 6 performs measurements of a width size of a pattern and a diameter of a contact hole formed on the semiconductor wafer 2 and inspections of a lack of the pattern, etc. as explained above.

Note that since the SEM testing device 6 is provided with the local vacuum formation portion 9 and a local vacuum region V is formed in a required minimum range for the tests and measurements, it is not necessary to place the whole testing apparatus 1 in a large vacuum chamber, etc.

Step 9: S9

The semiconductor wafer 2 subjected to predetermined tests and measurements by the SEM testing device 6 is conveyed by the conveying means 3 to a position facing to the outward form testing device 7.

Step 10: S10

The outward form testing device 7 observes the whole semiconductor wafer 2 to inspect particles, scratches, unevenness, etc. which are hard to be found by microscopic tests, such as the SEM testing. The wafer cassette is removed from the testing apparatus 1 and transferred by a suitable transfer means to the next process of the semiconductor wafer 2.

Note that the above order of tests and measurements is one example and can be naturally changed in accordance with testing processes required in respective production stages of the semiconductor wafer 2. Also, an arrangement of the respective testing devices 4, 5, 6 and 7 is shown in FIG. 1, but this is an example of the case where the tests and measurements by the respective testing devices 4, 5, 6 and 7 are performed in the above order and the order of the arrangement is not limited to this.

Since the conveying portion 3 is arranged to face the respective testing devices 4, 5, 6 and 7 in the above testing apparatus 1, a plurality of desired tests processes can be performed only by loading the semiconductor wafer 2 on one conveying portion 3, so that it contributes to make the apparatus compact. Furthermore, by aligning the semiconductor wafer 2 with the conveying portion 3 after loading the semiconductor wafer 2 on the conveying portion 3, the semiconductor wafer 2 is also aligned to the respective testing devices 4, 5, 6 and 7, consequently, alignment for each of the testing devices 4, 5, 6 and 7 is not necessary and a time for the testing process can become short.

Also, conveying of the semiconductor wafer 2 between the testing devices 4, 5, 6 and 7 can be handled only by the conveying portion 3, so that loading and alignment for exclusive conveying means every time the semiconductor wafer 2 is conveyed to each of the testing devices 4, 5, 6 and 7 become unnecessary and a TAT (turn around time) can be made short.

Furthermore, since the local vacuum formation portion 9 is provided to the SEM testing device 6, not only it becomes unnecessary to place the SEM testing device 6 in a local vacuum region (in a vacuum chamber), but it becomes unnecessary to place the whole testing apparatus 1 in a local vacuum region. Thus, a load lock chamber which has been conventionally required also becomes unnecessary and it contributes to make the testing apparatus 1 compact and shortens the TAT (turn around time) by that much.

Also, the SEM testing device 6 is not limited by a size, etc. of a test subject and can be freely arranged in a production line of the test subject due to the provision of the local vacuum formation portion 9 other than being used as one of a variety of testing devices in the testing apparatus.

Below, modification examples of the testing device using a scanning electron microscope of the present invention will be explained. Note that the configuration of local vacuum formation portions in the following modification examples is just the same with the configuration of the above local vacuum formation portion 9 and a detailed explanation thereof will be omitted.

Figure 4:
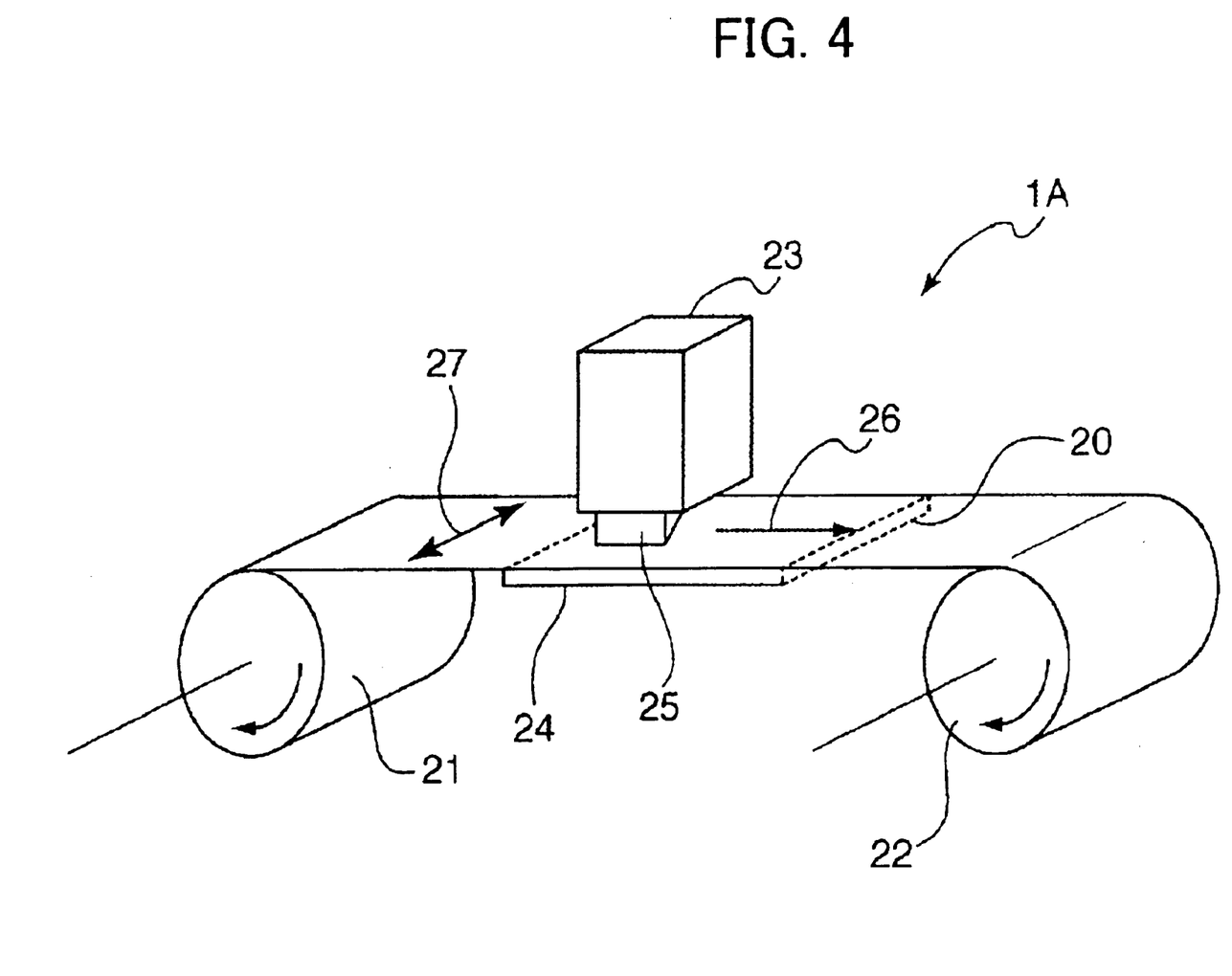
FIG. 4 is a perspective view schematically showing a first modification example of a testing device using a scanning electron microscope according to the present invention.

FIG. 4 is a first modification example of the testing device using the scanning electron microscope according to the present invention. Note that a testing apparatus 1A according to the modification example (hereinafter, simply referred to as a "testing device") performs tests and measurements on a rolled steel plate 20 as one of test subjects, which cannot be handled by a testing device using a conventional SEM wherein a vacuum chamber is used, by using a SEM and a local vacuum formation portion. The above rolled steel plate is a precision laminar steel plate, etc., for example used as a lead frame of a semiconductor.

The testing apparatus 1A comprises, as shown in FIG. 4, a conveying means composed of a feed roll 21 and a take-up roll 22 for conveying the rolled steel plate 20 having a length of several hundreds of meters, a SEM testing device 23 and a receiving plate 24 as a member arranged on a portion facing to the SEM testing device 23 for receiving the test subject.

The above SEM testing device 23 comprises a local vacuum formation portion 25 arranged on the side facing to the rolled steel plate 20, and the above receiving plate 24 holds the rolled steel plate 20 successively moving from the feed roll 21 to the take-up roll 22 in a state of facing to the local vacuum formation portion 25 of the SEM testing device 23.

Accordingly, in the testing apparatus 1A, by running the rolled steel plate 20 wound by the feed roll 21 in the direction indicated by an arrow 26 by winding by the take-up roll 22 in a state being sandwiched by the local vacuum testing device 25 and the receiving plate 24, a surface texture test by using the SEM testing device 23 can be successively performed. Also, by making the SEM testing device 23 or the feed roll 21 and the take-up roll 22 movable in the direction of an arrow 27, which is an orthogonal direction to the arrow 26, the whole surface of the rolled steel plate 20 can be a range able to be tested.

Also, in the same way as in the SEM testing device 6 of the testing apparatus 1, in the SEM testing device 23 of the testing apparatus 1A, it is configured that the SEM body and the local vacuum formation portion 25 are connected by a not shown extendable connector and the local vacuum formation portion 25 floats above the successively moving rolled steel plate 20 by a float means, so that a beam is able to scan the surface of the rolled steel plate 20 while floating above and follow fine relief shapes patterns on the surface of the rolled steel plate 20. Thus, highly accurate tests and measurements can be performed.

Note that since a vacuum chamber, etc. was used in a conventional testing device, the only way to test the rolled steel plate 20 was to test by cutting a part thereof as a test sample. However, in the testing apparatus 1A, an overall surface of a long rolled subject having a several hundreds of meters, such as the above rolled steel plate 20, can be tested without cutting a part thereof.

Figure 5:
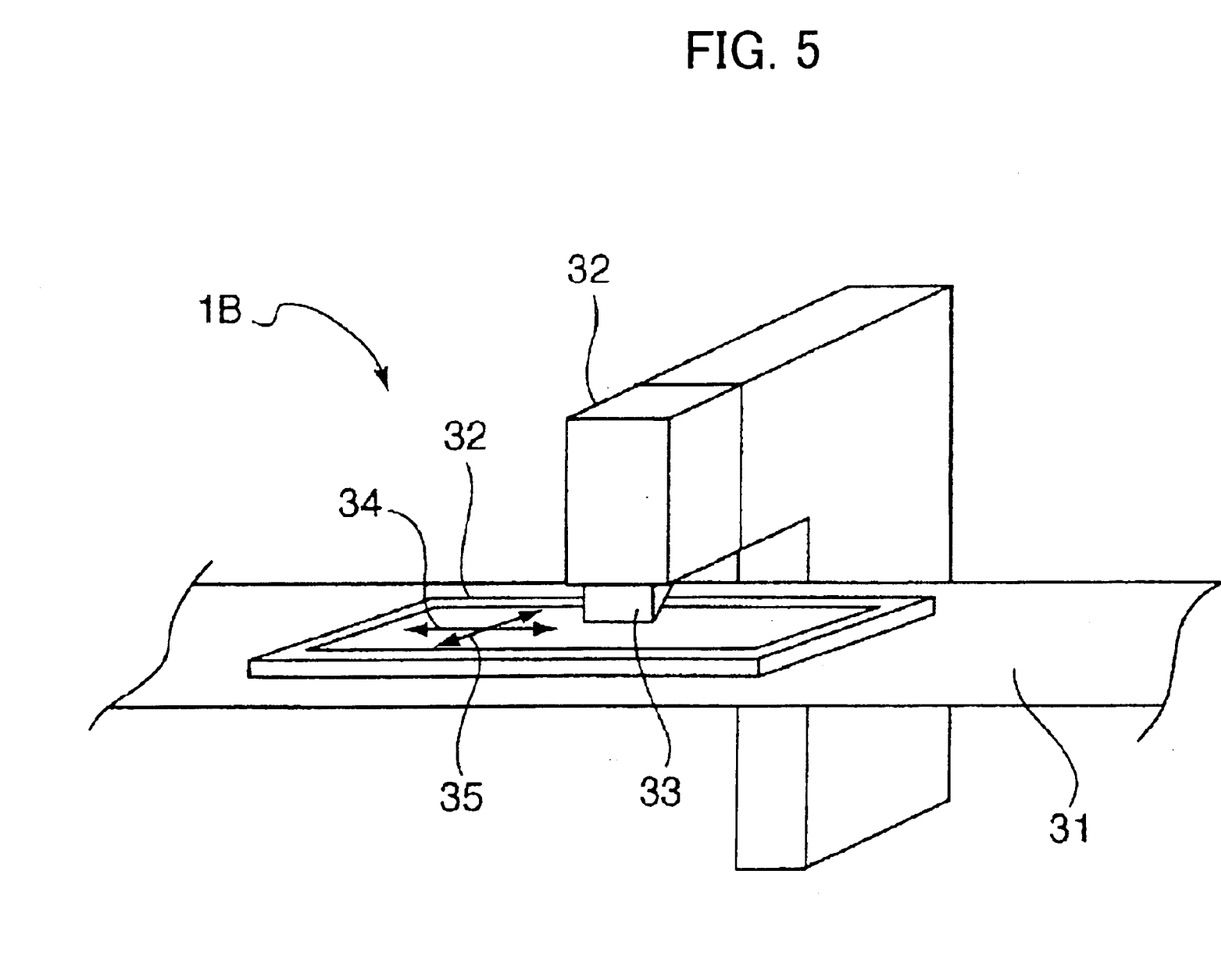
FIG. 5 is a perspective view schematically showing a second modification example of a testing device using a scanning electron microscope according to the present invention.

FIG. 5 is a second modification example 1B of a testing device using a scanning electron microscope according to the present invention. Note that the testing apparatus using a scanning electron microscope (hereinafter, simply referred to as a "testing device") 1B is for performing tests and measurements on a large-scale liquid crystal substrate 30 having a size in the longitudinal direction of 700 mm or more as one of test subjects which cannot be handled by a testing device using a conventional SEM which uses a vacuum chamber.

The testing apparatus 1B comprises, for example as shown in FIG. 5, a conveying portion 31 for conveying a liquid crystal substrate 30 and a SEM testing device 32. The above SEM testing device 32 comprises a local vacuum formation portion 33, etc. arranged on the side facing to the liquid crystal substrate 30.

Accordingly, in the testing apparatus 1B, a surface texture test using the SEM testing device 32 can be successively performed by moving the liquid crystal substrate 30 by the conveying portion 31 in the direction indicated by an arrow 34. Also, by making the SEM testing device 32 or the conveying portion 31 movable in the direction indicated by an arrow 35 which is an orthogonal direction with respect to the arrow 34, the overall surface of the liquid crystal substrate 30 can be a range able to be tested.

Also, in the same way as in the SEM testing device 6 of the testing apparatus 1 and the SEM testing device 23 of the testing apparatus 1A, in the above SEM testing device 32, since it is configured that a SEM body and the local vacuum formation portion 33 are connected by a not shown extendable connection means and the local vacuum formation portion 33 floats above the successively moving liquid crystal substrate 30 as a test subject by a float means, a beam is able to scan the surface of the liquid crystal substrate 30 while floating and follow fine relief shapes patterns on the surface of the liquid crystal substrate 30. Thus, highly accurate tests and measurements can be performed.

Furthermore, since a vacuum chamber, etc. was used in the conventional testing device, the only way to test the liquid crystal substrate 30 was to test by cutting a part thereof as a test sample, but in the testing apparatus 1B, even the overall surface of a large scale test subject, such as the above liquid crystal substrate 30, which cannot be held in a conventional vacuum chamber can be tested without cutting a part thereof.

Also, the local vacuum formation portions 9, 25 and 33 used in the testing apparatuses 1, 1A and 1B can be used in other way than being used by being combined with the SEM body. Below, types of usage of the local vacuum formation portion other than in a testing device will be explained.

Figure 6:
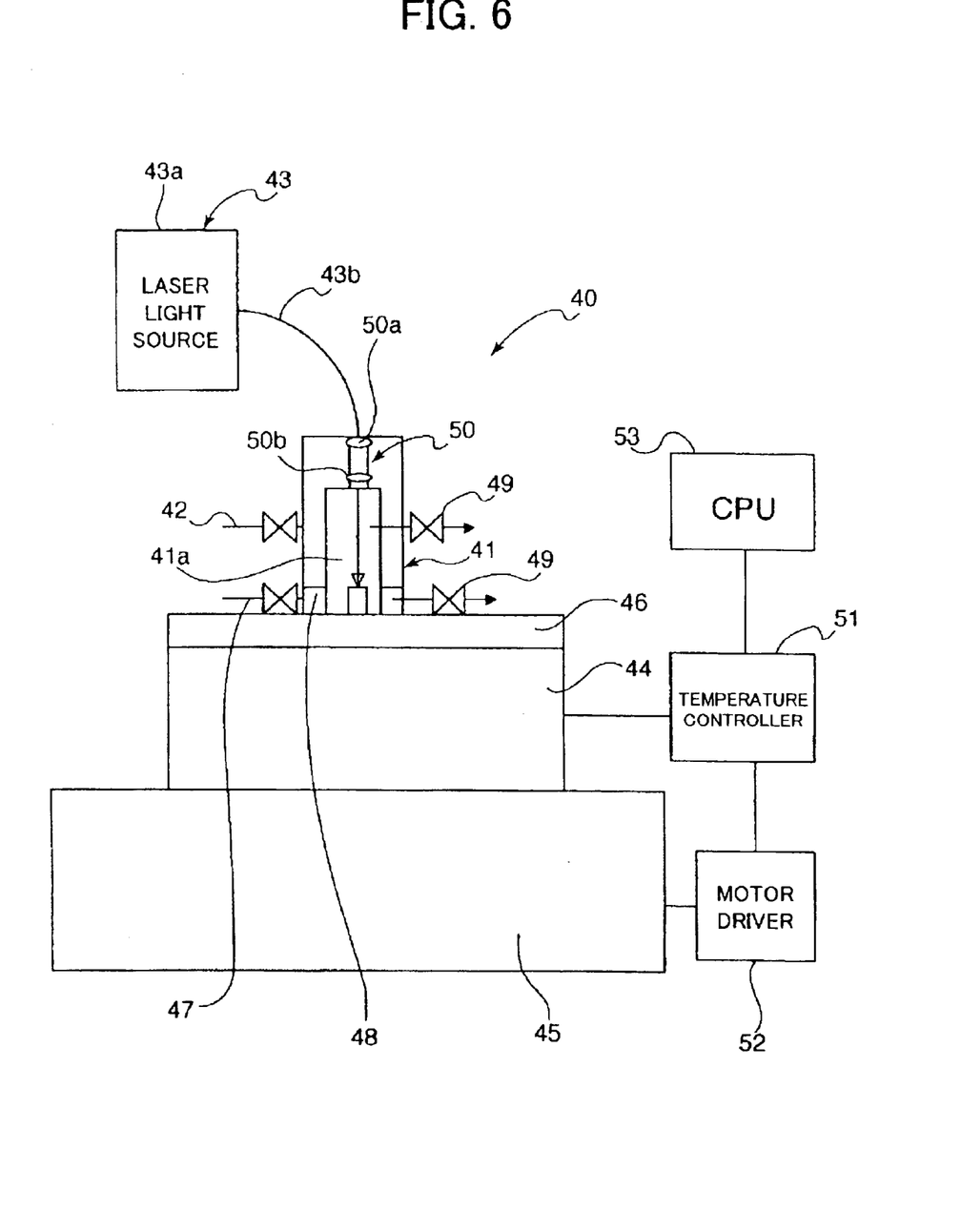
FIG. 6 is a schematic view of a film formation device for forming a thin film locally on a test subject by using a local vacuum formation portion.

FIG. 6 shows a film formation apparatus 40 for locally forming a thin film, etc. (to adhere a thin film or fine particles. Hereinafter, simply referred to as a "thin film") on a test subject (a semiconductor wafer, liquid crystal substrate, etc.) subjected to tests and measurements by a testing device using a scanning electron microscope according to the present invention explained above. The film formation apparatus 40 brings only a relevant part of the test subject (hereinafter, referred to as a "workpiece") to be formed a thin film by using the local vacuum formation portion to be in a vacuum state, seals a gas compound including constituting elements of film forming materials in a space in the vacuum state and supplies a reaction energy, such as a light, heat and plasma, etc., only to the film formation part to bring chemical reactions, so that a thin film is formed locally.

Namely, the film forming apparatus 40 comprises, as schematically shown in FIG. 6, a local vacuum formation portion 41 for locally forming a highly vacuum state, a gas introduction portion 42 for introducing a gas compound to be thin film materials (hereinafter, referred to as a "process gas") to a space made to be in a vacuum state by the local vacuum formation portion 41, an energy supply portion 43 for supplying reaction energy for bringing chemical reactions to the gas compound and the workpiece, a base 44 having a temperature adjustment function for promoting the above chemical reactions and an aligning portion (X–Y stage) 45 for accurately aligning a position of the film formation part of the workpiece and locally forms a thin film on the workpiece 46.

Conventionally, when forming a thin film on a workpiece, such as a semiconductor wafer and a liquid crystal substrate, in a vacuum state, a workpiece is sealed in a vacuum chamber, a gas compound including constituting elements of thin film materials is introduced to the vacuum chamber, and chemical reactions are brought on the surface of the workpiece, etc. However, when forming a film only on a part of the workpiece, that is locally, it was not possible to form a film locally, and it was necessary to seal the whole workpiece in a vacuum chamber, to form a film allover the workpiece and to remove on unnecessary parts by etching processing in a later process. However, it becomes possible to locally form a thin film, etc. on a workpiece by using the above film forming apparatus 40.

The above local vacuum formation portion 41 comprises a float portion 48 for floating the whole workpiece 46 by a compressed gas supplied form a compressed gas supply portion 47 for supplying an inert gas, etc. and two exhaust portions 49 and 49 for forming a local vacuum region inside 41a and separating the local vacuum region from the outside under an atmosphere pressure.

Accordingly, the local vacuum formation portion 41 can freely move above the workpiece 46 to a desired film formation part without contacting to damage the surface of the workpiece 46, while maintaining a high vacuum state of the inside 41a.

Also, the inside 41a of the local vacuum formation portion 41 in a vacuum state is supplied a process gas to be materials of a thin film or fine particles by a gas introduction means 42.

The energy supply portion 43 comprises a laser light source 43a for generating a deep ultraviolet ray, an optical fiber 43b and an optical system 50, etc. Accordingly, the deep ultraviolet ray emitted from the laser light source 43a is supplied to the inside 41a of the local vacuum formation portion 41 by the optical fiber 43b and converged to irradiate a film formation portion of the workpiece 46 by lenses 50a and 50b of the optical system 50. Accordingly, the process gas is chemically reacted by energy of the deep ultraviolet ray and a thin film is formed locally on the surface of the workpiece 46.

The base 44 fixes the workpiece 46 by a not shown fixing means and heats the workpiece 46 to be a temperature for easily promoting the chemical reactions of the process gas.

A temperature controller 51 controls an operation of a not shown heating means of the base 44 for the workpiece and a motor driver 52 controls an operation of a not shown motor for driving an alignment portion 45.

A timing of supplying the process gas by the gas introduction means 42 and an operation of the two exhaust portions 49 and 49 can be directly controlled by the control portion 53. Also, controlling of the temperature of the base 44 and a position of the alignment portion 45 are controlled by a control portion 53 via the temperature controller 51 and the motor driver 52.

In the film forming apparatus 40 having the configuration as explained above, a thin film is locally formed on a desired portion of the workpiece 46 in an order described below.

(1) A workpiece 46 is fixed on the base 44

(2) An inert gas is supplied from the compressed gas supply means 47 to the inside 41a of the local vacuum formation portion 41, the inside 41a is separated from the outside and the local vacuum formation portion 41 is slightly floated above the workpiece 46.

(3) The alignment portion 45 aligns a desired film formation part of the work piece 46 with the local vacuum formation portion 41.

(4) Two exhaust portions 49 and 49 are operated to bring the inside 41a to be in a highly vacuum state.

(5) The process gas is supplied to the inside 41a of the local vacuum formation portion 41 in a vacuum state by the gas introduction portion 42.

(6) The energy supply portion 43 is operated to irradiate a deep ultraviolet ray emitted from the laser light source 43a to an optical system through the optical fiber 43b, and the lenses 50a and 50b converge the ray to the film formation part of the workpiece 46 for irradiating with predetermined intensity for a predetermined time.

(7) The process gas in the local vacuum formation portion 41 is brought to chemically react by energy of the deep ultraviolet ray, and a thin film is formed on the film formation part of the workpiece 46.

(8) Operations of the exhaust portions 49 and 49, the gas introduction means 42 and the energy supply portion 43 are stopped and the procedure from the above (3) to (6) is repeated to form a thin film on another film formation part on the workpiece 46. Alternately, when finishing the film formation operation on the workpiece 46, operations of all portions in the film forming apparatus 40 are stopped and the workpiece is removed from the base 44.

As explained above, according to the film forming apparatus 40, it is possible to locally form a thin film freely on any part of the workpiece 46, furthermore, by partially changing film forming conditions, it is also possible to form a thin film, wherein different kinds of thin films are integrally formed, on the workpiece 46 and to form different kinds of thin films on different parts in the same process. Thus, the TAT in the process development can be made short. Also, in the case where the workpiece 46 is a liquid crystal substrate and a film forming apparatus 40 is used in the production processes, a partial repair on a pixel defect part becomes possible, so that the yields can be improved.

Also, in the film forming apparatus 40, it is possible to form films of partially different film forming conditions on a workpiece in the same process, so that the production processes can be reduced.

Furthermore, in the film forming apparatus 40, a vacuum state can be locally formed by using the local vacuum formation portion 41, so that a time required for vacuuming can be largely reduced comparing with the case of using a vacuum chamber.

Note that the shapes and configurations of the respective portions described in the above embodiments are just examples of embodiments in implementing the present invention and a technical scope of the present invention may not be taken in a limited way.

INDUSTRIAL APPLICABILITY

As explained above, since a testing device using a scanning electron microscope according to the present invention comprises a local vacuum formation portion, it is not necessary to hold the whole testing device in a vacuum chamber, etc. and a conventionally required load lock chamber becomes also unnecessary, so that it contributes to make the testing device compact. Also, vacuuming of the vacuum chamber or load lock chamber becomes unnecessary, so that the TAT (turn around time) can be reduced by that much. Furthermore, since it can be freely placed on a production line, etc. of a test subject other than being used as one of a variety of testing means in a complex testing device having a variety of testing means, consequently, it is applicable as a testing device of a testing apparatus for performing a variety of tests in production processes of, for example, a semiconductor wafer and liquid crystal substrate, etc. in a nondestructive way.

What is claimed is:

1. A testing device using a scanning electron microscope comprising a scanning electron microscope for performing tests and measurements on any part of a test subject by irradiating an electron beam emitted from the scanning electron microscope on at least a portion of the test subject, wherein:

the device comprises a local vacuum formation portion for locally forming a vacuum region by blocking at least a portion of said test subject from outside air; and said local vacuum formation portion comprises an exhaust means for exhausting to form a partial vacuum region, a float means for floating the whole local vacuum formation portion apart from the test subject by emitting a compressed gas to an outer circumference portion of the local vacuum formation portion, and further comprising a a distance measuring means for measuring a distance from the test subject for controlling floating of the local vacuum formation portion.

2. A method for testing a device comprising:

forming a local vacuum by blocking at least a portion of said test subject from outside air, floating the whole local vacuum formation portion apart from the test subject by emitting a compressed gas to an outer circumference of a region of the local vacuums; and measuring distance from the test subject.

3. The method of claim 2, wherein the step of measuring comprises measuring a distance from an electron microscope to the device under test and further comprising irradiating the device under test using the electron microscope.

* * * * *

UNITED STATES PATENT AND TRADEMARK OFFICE
CERTIFICATE OF CORRECTION

PATENT NO. : 6,953,939 B2  
APPLICATION NO. : 10/472312  
DATED : October 11, 2005  
INVENTOR(S) : Tetsuo Abe et al.

Page 1 of 1

It is certified that error appears in the above-identified patent and that said Letters Patent is hereby corrected as shown below:

Title page, item should read  
--(73) Assignee: (1) SONY CORPORATION, Tokyo (JP), and  
                   (2) JEOL LTD, Tokyo (JP)--

Signed and Sealed this

Sixth Day of March, 2007

JON W. DUDAS  
*Director of the United States Patent and Trademark Office*